United States Patent [19]
Madsen

[11] 3,971,136
[45] July 27, 1976

[54] HYGIENIC SPRAY APPARATUS

[76] Inventor: Erik H. Madsen, 3230 S. 9th East, Salt Lake City, Utah 84106

[22] Filed: May 16, 1974

[21] Appl. No.: 470,365

[52] U.S. Cl. .................................................. 32/58
[51] Int. Cl.² ........................................ A61C 3/10
[58] Field of Search ............. 32/58, 89; 128/62 A; 239/308, 321; 51/12, 11, 8

[56] References Cited
UNITED STATES PATENTS

| | | | |
|---|---|---|---|
| 1,664,369 | 3/1928 | Maurer | 32/58 |
| 2,661,537 | 12/1953 | Angell | 32/58 |
| 2,696,049 | 12/1954 | Black | 32/58 |
| 3,080,154 | 3/1963 | Tanner | 239/321 |
| 3,205,620 | 9/1965 | Woodworth et al. | 51/8 |
| 3,276,168 | 10/1966 | Ashworth | 51/11 |
| 3,344,524 | 10/1967 | Kulischenko | 32/58 |
| 3,407,539 | 10/1968 | Ashworth | 51/11 |
| 3,559,344 | 2/1971 | Petersen | 51/11 |
| 3,752,404 | 8/1973 | Forsberg | 239/308 |
| 3,828,478 | 8/1974 | Bemis | 51/11 |

*Primary Examiner*—Robert Peshock
*Attorney, Agent, or Firm*—B. Deon Criddle

[57] ABSTRACT

Apparatus for containing and pressure spraying hygienic slurries, and then in a manner such that slurry particles are maintained in solution immediately prior to and at force feeding the same to a jet spray nozzle. Aerator means may be used to maintain particulates in suspension and, simultaneously, to develop an air pressure head for forcing the slurry out of its container toward the applicator. Various means are shown and described for maintaining slurry particles in suspension as well as for supplying under pressure such slurry to an applicator.

6 Claims, 7 Drawing Figures

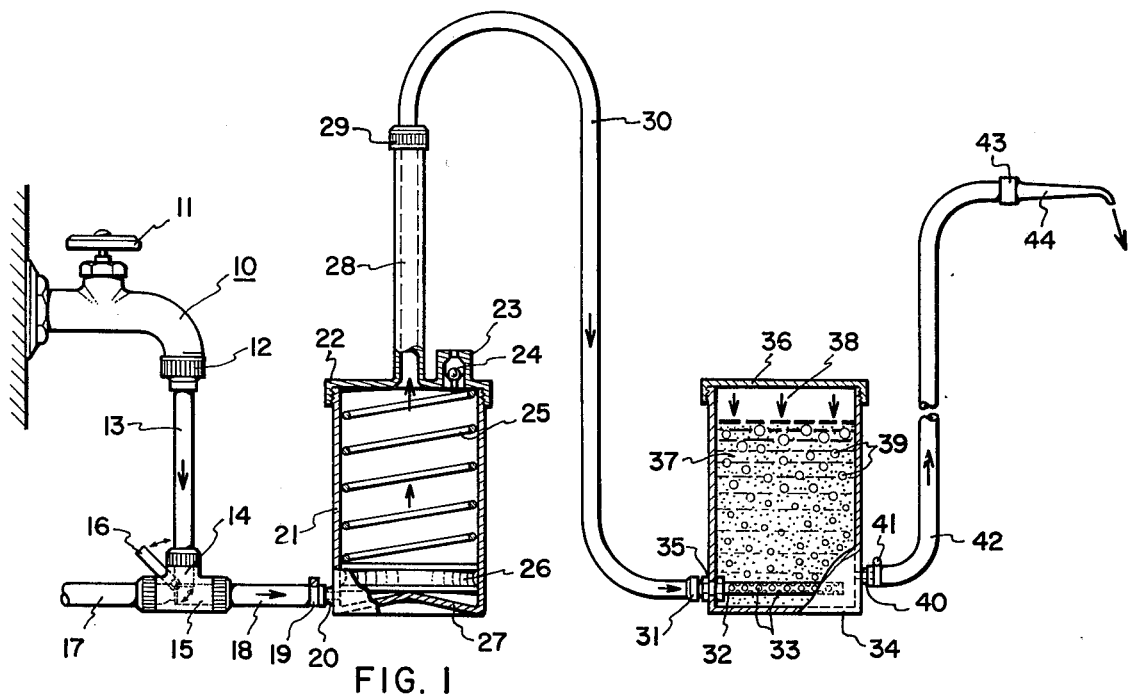
FIG. 1
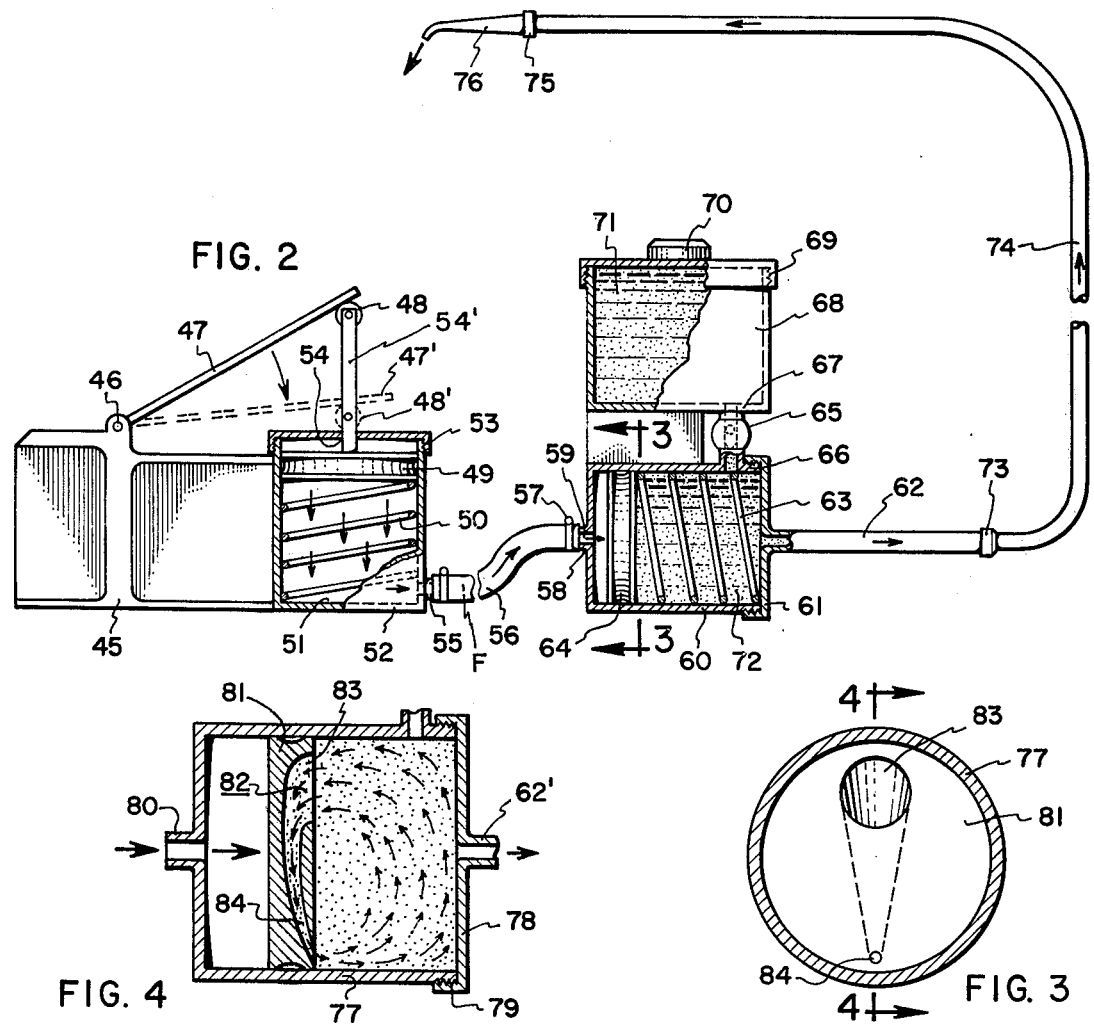
FIG. 2
FIG. 4
FIG. 3

3,971,136

HYGIENIC SPRAY APPARATUS

The present invention relates to spray apparatus and, more particularly, to spray apparatus suitable for storing and dispensing slurries in a relatively high pressure spray.

The present invention finds particular and unique application to the cleaning of teeth and, more particularly, to the removal of plaque therefrom.

Reduced to simplest terms, the plaque matrix which forms as an undesired layer over teeth has a constituency and chemical nature which renders the plaque highly permeable to non-polar molecules such as sugars but not permeable to polar molecules such as acids and bases.

As to chemical reaction, sugars present in the mouth pass through the matrix of the plaque and are metabolized by plaque bacteria into lactic acid. This lactic acid is thus in proximity with tooth materials proper as well the gums and cannot escape unless and until the plaque is removed. This acid has the ability actually to dissolve tooth materials, and likewise the ability to burn severely the gum tissues. There likewise may be other kinds of acids formed in the plaque which react against the tooth; however, lactic acid is believed to be the principal constituent.

The intimate presence of lactic acid with the crown and root materials of the tooth, as well as the surrounding gums, causes extensive damage, including not only dental caries but also gum inflammation called gingivitis; this latter condition, if left unchecked, can become very serious. Indeed, rheumatic heart disease, as well as other heart maladies, are often attributable to poor dental hygiene.

The standard tooth-brush is really quite difficult to use, from a scientific point of view, in order to assure the total removal of foreign matter, e.g. food particles and the like, as well as plaque from the tooth.

The present invention provides apparatus constructed to provide a high-pressure slurry jet or spray which, at suggested operating pressures of from 15 - 60 p.s.i., will effectively penetrate fluid boundary layers as well as the plaque itself, tending to leave the sole sprayed teeth unusually clean.

The subject spray equipment can be used in homes and in schools as well as in dental offices and hospitals.

The apparatus as constructed utilizes little or no valving means so far as the slurry utilized is concerned. In brief, the invention comprises apparatus constructed to pressurize a suitable slurry for jet application to teeth, and this optionally using a selectible, alternative, waterspray source. The slurry is aerated or otherwise conditioned by the structure such that the slurry particles are maintained essentially in total suspension. Air pressure or other means force the slurry through the conduit to a terminal nozzle; the structure is likewise designed for remote operation.

Accordingly, a principal object of the present invention is to provide apparatus for dispensing slurries under pressure.

A further object is to provide a slurry jet structure.

An additional object is to provide apparatus for maintaining slurry particles in suspension in their respective slurry solutions prior to and during actual usage.

An additional object is to provide apparatus for spraying the oral cavity, including teeth, with a pressured slurry solution.

An additional object is to provide for the remote actuation of stored slurries.

An additional object is to provide apparatus for maintaining, in slurry pressure cylinders, slurry particles therein in suspension in their liquid carriers.

The features of the present invention which are believed to be novel are set forth with particularity in the appended claims. The present invention, both as to its organization and manner of operation, together with further objects and advantages thereof, may best be understood by reference to the following description, taken in connection with the accompanying drawings in which:

FIG. 1 is a side elevation, partially sectioned, of structure comprising one form of the present invention.

FIG. 2 is a side elevation, partially broken away in section, of alternate structure similar to that shown in FIG. 1.

FIG. 3 is an enlarged transverse vertical section taken along the line 3-3 in FIG. 2.

FIG. 4 is a vertical section taken along the line 4-4 in FIG. 3.

Figure 5:
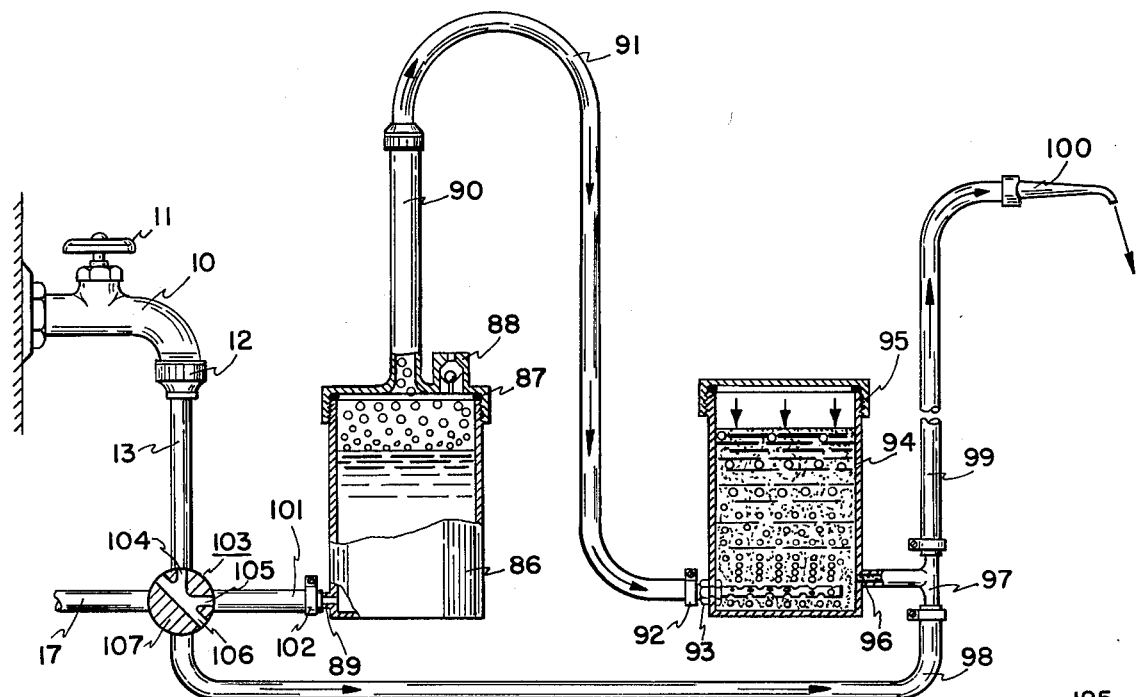
FIG. 5 illustrates in side elevation, and in fragmentary section, an additional embodiment of the present invention.

In FIG. 1 a water tap 10 is provided with a valve handle 11 and includes a threaded outlet portion to which connector 12 of conduit 13 is threaded. The bottom portion of conduit 13 is coupled to a tee 15, the same incorporating a valve 14 provided with valve handle 16. The tee valve construction is conventional and provides for flow of water from conduit 13 to conduit 18, in the direction of the arrows, as well as the exhaust of fluid in a direction to the left in conduit 18 and out drain conduit 17. Conduits 17 and 18 are connected as shown to opposed legs of the tee. Connector 19 of conduit 18 is coupled to inlet 20 of air compression cylinder 21. The latter is provided with a cover 22 having riser 28 and also air bleeder valve 23 having valve ball 24.

A spring 25 is disposed within the cylinder 21 and abuts against the upper surface of air compression piston 26. Bottom 27 may be concave downwardly if desired and abuts the bottom surface of piston 26. Connector 29 of curved conduit 30 is coupled to riser 28; the remaining connector 31 of conduit 30 is connected to aerator tube 32. The latter is disposed at the bottom of pressure exhaust cylinder 34. Suitable attachments 35 mount the aerator tube 33 in a position as shown such that connector 31 may be coupled thereto.

Slurry outlet port 40 of cylinder 34 receives connector 41 of conduit 42. The latter is designed as a flexible elongate conduit having the outer end thereof connected to boss 43 of spray nozzle 44.

In the structure shown in FIG. 1, the slurry intended for use is positioned at 37 and the cover 36 installed. The tap 10, in being connected to conduit 13, will provide a pressured water flow to the under surface of piston 26, this upon the proper setting of valve handle 16. Thus, water pressure on the underside of piston 26 forces piston 26 upwardly against compression spring 25. This action serves to compress the air within the volume of cylinder 21 above piston 26, this such that compressed air is forced through the curved conduit 30 and through aerator 32 at holes 33/ Air bubbles therefrom at 39 proceed upwardly to aerate the slurry and thus to keep slurry particles in suspension. Air pressure builds up at 38, see the arrows, so as to force the slurry downwardly through outlet port 40 and into conduit 42. The slurry, as agitated by the air bubbles 39, thence proceeds from conduit 42 out of the nozzle 44 to accomplish the spraying purposes intended, whereupon, on the completion of the spraying operation, the water tap 10 is closed by valve 11 and valve handle 16 reversed such that drainage may proceed in a reverse direction, from the bottom side of piston 26 through conduit 18 and 17, thereby draining the system of water. At this point in time the bleeder valve at 23,24 opens so as to supply a new charge of air into the cylinder and conduit 30.

In the structure shown in FIG. 2, a housing 45 is provided with an upstanding ear receiving pivot pin 46; the latter forms a part of foot control 47 which is held upwardly by idler wheel 48 pinned to piston rod 54'. Piston rod 54' proceeds upwardly from piston 49. Cover 53 includes the aperture 54 for receiving the piston rod. Suitable packing gland or other means may be provided at the aperture 54 as desired. Spring 50 backs piston 49 and is seated in the bottom of piston 52 to rest against bottom surface 51. Outlet port 55 of cylinder 52 receives a connection end of conduit 56, and the remaining end thereof is beveled to inlet port 58 which includes inlet passageway 59. Cylinder 60 is provided with a cover 61 threaded onto one end thereof. The latter is provided with a riser 62 having its outer end secured to connector 73 of conduit 74. The latter in turn is connected to the receiving end or boss 75 of spray nozzle 76. Slurry at 72 is disposed within a cylinder as shown; the same is provided by the slurry feed stock 71 disposed in slurry tank 68. Tank 68 is provided with a cover 69 having actuating knob 70. The bottom 67 of the tank is apertured so as to provide for connection of a check valve 65 between the same and inlet port 66. Cylinder 77 is provided with a cover 78 having annular flange 79 in threaded engagement with such cylinder. Cylinder 77 is alternate to cylinder 60 in FIG. 2, and will be understood to include the spring 73 as well. FIGS. 3 and 4, however, indicate that the piston may be constructed to provide a passageway 82 having a large orifice 83 and also a small return orifice at 84. The purpose for the design of the passageway of piston 81 in FIG. 4 is to insure a swirling action, due to different flow speeds at the respective orifices 83 and 84, as shown by the arrows, this so that there will be a natural agitation of the slurry as the same is urged forwardly toward riser 62', thereby tending to maintain particles in the slurry in suspension. FIG. 3 indicates large and small aperture arrangement at 83 and 84 so as to effect such swirling action. For convenience of illustration the spring 63 in FIG. 2, while intended also for inclusion in the structure of FIG. 4, is not shown in FIG. 4 for purposes of clarity.

The structure of FIGS. 2-4 operates as follows: Depression of the foot peddle 47 will cause a depression of piston rod 54' and of piston 49 against spring 50. The interior of cylinder 52 beneath piston 49 will be filled with a pneumatic or hydraulic fluid F, operating to pass through conduit 56 and positively displace piston 64 to the right. The slurry reservoir 68 supplies slurry into that interior portion of cylinder 50 which is disposed to the right of piston 64. Accordingly, the movement of piston 64 to the right will effect a squeezing out of the slurry and, hence, a forward urging thereof through risers 62, conduit 74, and through the nozzle 76. Accordingly, it is seen that the slurry pressure cylinder 60 may be actuated remotely by a foot pedal construction as shown to the right of FIG. 2. Conduit 56 may be made as long as is desired to effect remote actuation of cylinder 60. Once the spraying action is completed the foot is raised, both springs return their pistons in the respective cylinders 60 and 52, so that the hydraulic or pneumatic fluid returns via conduit 56 into the interior of cylinder 52.

In FIG. 5 a slightly different construction is shown. This time the water tap 10 is coupled by connector 12 and conduit 13 to a distribution valve 103, the latter being provided with port passages 104-106 and the revolvable valve gate 107. Drain conduit 17 as well as inlet conduit 101 are connected as shown, with an additional conduit 98 leading to tee 97 in a manner as hereinafter described. Cylinder 86 receives water from the tap 10 via valve 103, permitting the water to compress the air contained in the cylinder at riser 90, and with such compressed air being routed through conduit 91 to the aerator tube contained within cylinder 94. The aerator tube shown, which will be similar to aerator tube 33 in FIG. 1, will cause the air bubbles 39 produced to keep slurry particles in suspension and at the same time admit the air to the upper portion of the cylinder so as to provide a downward driving force as shown on the fluid level contained within cylinder 94. This then supplies pressure to exhaust the slurry through tee 97 and the conduit and nozzle 99 and 100 connected thereto. If it is desired to rinse the working surfaces after the slurry has been applied, then the valve 103 is simply reversed so that water will flow from conduit 13 directly into conduit 98 and tee 97 and from thence to the nozzle. In the event of a draining that will be needed following slurry application, the valve 103 will be conditioned so that a reversal occurs in a direction to the left relative to conduit 101 and drain conduit 17.

Figure 6:
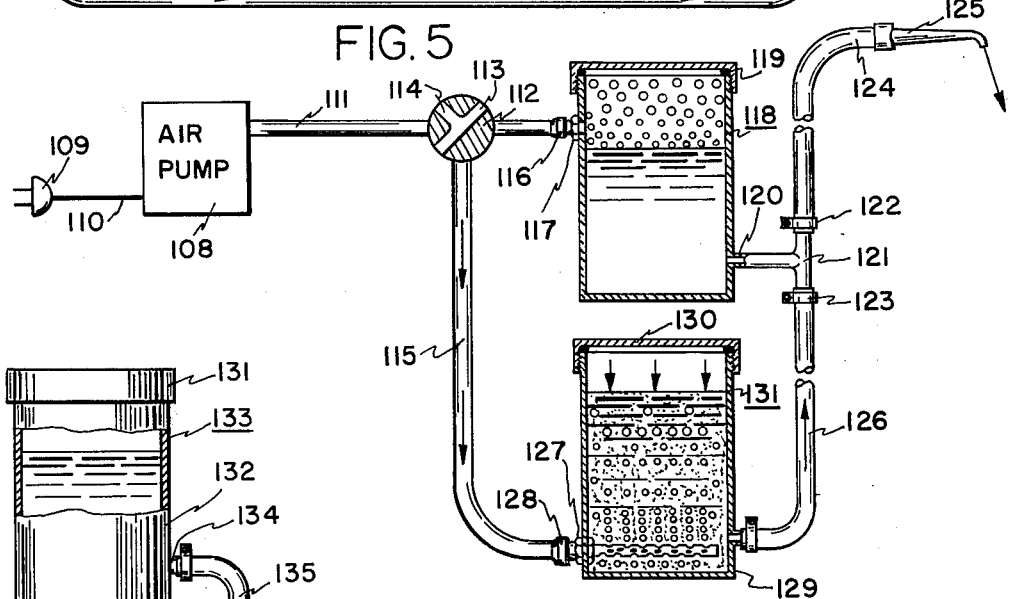
FIGS. 6 and 7 illustrate apparatus systems wherein both water and slurry liquids may be used alternately, the same being powered either by an air pump or by a centrifugal pump.

In FIG. 6 air pump 108 is provided with plug 109 and leads 110, the air pump generating air into conduit 111. Valve means 112 includes passagesways 113 and 114 in the manner shown relative to three-way valves, this so that air may be supplied alternately to cylinder 118 and also cylinder 131. These cylinders are provided with covers 119 and 130 in the manner indicated. Conduit 115 and 116 are connected in the manner shown to inlet ports 117 and 127, the latter by conduit connector 128. The bottom portion of cylinder 131 is provided with aerator tube 132. Conduit 120 forms part of a tee 121 to which is attached the connectors 122 and 123 of conduit 124 and 126, respectively. The supply end of conduit 126 is connected to and forms communication with the cylinder 131 in the manner shown. Nozzle 125 is of course supplied the elongate flexible conduit 124.

In FIG. 6 the air pump supplies compressed air either to the water containing cylinder 118 or to the aerator 32 of slurry-containing cylinder 131. The valve 112 of course will determine which of the two cylinders is used for supplying a fluid media to the riser 125.

Figure 7:
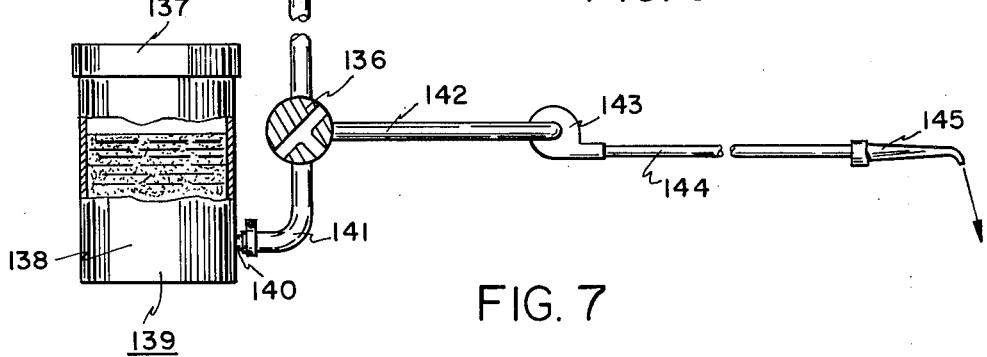

In FIG. 7 containers 133 and 139 include vessels 132 and 138, having covers or caps 131 and 137 as shown. Outlet conduit 135 and 141 are connected to respective outlet ports 134 and 140. Such conduit leading to valve 136. The same comprises a three-way valve wherein the water media contained in 133, or the slurry media contained in the container 139 is fed by the valve to a centrifugal pump 143. The latter includes an inlet conduit 142 connected to the valve as shown. Outlet conduit 144 is coupled to the centrifugal pump 143, is elongate and flexible by design, and is connected to nozzle 145.

In FIG. 7 the operation is as follows: A solution from the slurry storage at 139 or simply clear water from the water storage at 133 is conveyed by the valve 136 to a centrifugal pump that supplies force to nozzle 145. Hence, a slurry solution followed by a water treatment may be effective by the structure of FIG. 7.

The subject apparatus is presented as useful for handling hygienic slurries to be described in a depending patent application. The particulates contained within a water carrier may comprise simply plastic particles of the order of 2 – 20 thousands of an inch in maximum dimension and exhibiting a surface hardness less than exterior tooth materials; nonetheless, such plastic particulates, in effect, will be abrasive as to plaque, to effect the removal thereof.

What is provided in all of the invention is a means whereby a slurry fluid, possibly alternated with or succeeded by a water-treatment fluid, may be applied to a pressure nozzle for cleaning the plaque from teeth, for example. In all of the embodiments shown, structure is provided whereby, either by direct or remote actuation, the fluid media utilized is pressured toward the nozzle or orifice means used.

While particular embodiments of the present invention have been shown and described, it will be obvious to those skilled in the art that changes and modifications may be made without departing from this invention in its broader aspects, and, therefore, the aim in the appended claims is to cover all such changes and modifications as fall within the true spirit and scope of this invention.

I claim:

1. Hygienic apparatus for spraying cleansing slurries which include minute plastic particles, said apparatus including, in combination: a closed, pressurized, container having a pre-mixed slurry therein, said slurry comprising a liquid carrier and plastic particles disposed therein, said container including an inlet, an outlet, and means for maintaining said particles in suspension in said carrier during slurry discharge through said outlet, for pressurizing said slurry within said container and for forcing a predetermined volumetric charge of said slurry through the outlet, a jettype discharge nozzle above said container, and a flexible elongate conduit coupled between said outlet and said nozzle.

2. Apparatus according to claim 1 wherein said means comprises an air pump and also an aerator tube disposed within said container and coupled to said air pump.

3. Structure according to claim 1 wherein said apparatus includes a water-pressure actuated air pump coupled to said slurry container, for supplying air pressure thereto.

4. Structure according to claim 1 wherein said container includes a piston with a passage therethrough as said means, and supplemental means for pressure-actuating said piston.

5. Apparatus according to claim 2 wherein said container is constructed as a closed pressure vessel whereby to permit pressured air, as delivered by said air pump to said aerator tube, to build up an air pressure head above said slurry for force-discharging said slurry through said outlet.

6. Structure according to claim 4 wherein said pressure-actuating supplemental means comprises hydraulic means remotely coupled to said container for supplying fluid pressure to said piston, said piston including a return spring.

* * * * *